(12) United States Patent
Kobayashi et al.

(10) Patent No.: US 10,765,387 B2
(45) Date of Patent: Sep. 8, 2020

(54) POSITION ADJUSTMENT DEVICE FOR FLAT PANEL DETECTOR, POSITION ADJUSTMENT METHOD FOR FLAT PANEL DETECTOR, AND RADIOTHERAPY APPARATUS

(71) Applicants: Toshiba Energy Systems & Solutions Corporation, Kawasaki-shi (JP); TOSHIBA PLANT SYSTEMS & SERVICES CORPORATION, Yokohama-shi (JP)

(72) Inventors: Takayuki Kobayashi, Itabashi (JP); Hiromasa Itoh, Yokohama (JP); Shigeru Kasai, Yokohama (JP)

(73) Assignees: Toshiba Energy Systems & Solutions Corporation, Kawasaki-shi (JP); TOSHIBA PLANT SYSTEMS & SERVICES CORPORATION, Yokohama-shi (JP)

( * ) Notice: Subject to any disclaimer, the term of this patent is extended or adjusted under 35 U.S.C. 154(b) by 0 days.

(21) Appl. No.: 16/232,240

(22) Filed: Dec. 26, 2018

(65) Prior Publication Data

US 2019/0192095 A1   Jun. 27, 2019

(30) Foreign Application Priority Data

Dec. 27, 2017   (JP) .................................. 2017-250940

(51) Int. Cl.
*A61B 6/00* (2006.01)
*G01T 1/16* (2006.01)
*A61N 5/10* (2006.01)

(52) U.S. Cl.
CPC .......... *A61B 6/4452* (2013.01); *A61B 6/4233* (2013.01); *A61B 6/4411* (2013.01); *A61B 6/587* (2013.01); *A61N 5/10* (2013.01); *A61N 5/1049* (2013.01); *G01T 1/16* (2013.01); *A61N 2005/1061* (2013.01)

(58) Field of Classification Search
CPC ........ A61B 6/587; A61N 5/10; A61N 5/1049; A61N 5/1061
See application file for complete search history.

(56) References Cited

U.S. PATENT DOCUMENTS

2013/0114790 A1* 5/2013 Fabrizio .................... A61B 6/02
378/62
2015/0352376 A1* 12/2015 Wiggers ................. A61B 6/545
250/252.1
2018/0064955 A1 3/2018 Iseki

FOREIGN PATENT DOCUMENTS

| CN | 105997109 A | 10/2016 |
|----|----|----|
| JP | 2008-456 A | 1/2008 |
| JP | 2009-150667 | 7/2009 |
| JP | 2010-178989 | 8/2010 |

(Continued)

*Primary Examiner* — Dani Fox
(74) *Attorney, Agent, or Firm* — Oblon, McClelland, Maier & Neustadt, L.L.P.

(57) ABSTRACT

A position adjustment device for a flat panel detector comprising: a guide that is provided on a surface side of the flat panel detector and can be measured by an optical device; and a fixing member configured to fix the guide to one of a side of the flat panel detector of a position adjustment unit and a side of a support portion for supporting the flat panel detector, the position adjustment unit being provided between the flat panel detector and the support portion.

11 Claims, 14 Drawing Sheets

(56) References Cited

FOREIGN PATENT DOCUMENTS

| | | |
|---|---|---|
| JP | 2011-92612 | 5/2011 |
| JP | 2012-37345 | 2/2012 |
| JP | 2016-221156 | 12/2016 |
| TW | I471152 B | 2/2015 |
| TW | 201706562 A | 2/2017 |
| WO | WO 2016/174872 A1 | 11/2016 |

* cited by examiner

POSITION ADJUSTMENT DEVICE FOR FLAT PANEL DETECTOR, POSITION ADJUSTMENT METHOD FOR FLAT PANEL DETECTOR, AND RADIOTHERAPY APPARATUS

CROSS-REFERENCE TO RELATED APPLICATION

This application is based upon and claims the benefit of priority from Japanese Patent Application No. 2017-250940, filed on Dec. 27, 2017, the entire contents of which are incorporated herein by reference.

FIELD

Embodiments described herein relate generally to a position adjustment device for a flat panel detector, a position adjustment method for a flat panel detector, and a radiotherapy apparatus.

BACKGROUND

Conventionally, a radiotherapy apparatus includes an X-ray tube for generating an X-ray image and a flat panel detector in order to check a position of a lesion area of a patient. In such a radiotherapy apparatus, there is a known technique in which positioning of various devices is performed with reference to a phantom disposed at the isocenter.

[Patent Document 1] Japanese Unexamined Patent Application Publication No. 2016-221156

In the technique described above, X-ray imaging is performed to generate an X-ray image depicting a phantom and the position of the flat panel detector is adjusted on the basis of this X-ray image.

However, there is a problem that work efficiency of the position adjustment of the flat panel detector is poor because it is necessary to alternately repeat the X-ray imaging and the movement of the flat panel detector until the flat panel detector is moved to a proper position.

In view of the above-described problem, an object of embodiments of the present invention is to provide such a position adjustment technique for a flat panel detector that work efficiency of position adjustment of a flat panel detector can be improved.

DETAILED DESCRIPTION

In one embodiment of the present invention, a position adjustment device for a flat panel detector comprising:

a guide that is provided on a surface side of the flat panel detector and can be measured by an optical device; and a fixing member configured to fix the guide to one of a side of the flat panel detector of a position adjustment unit and a side of a support portion for supporting the flat panel detector, the position adjustment unit being provided between the flat panel detector and the support portion.

According to embodiments of the present invention provide to such a position adjustment technique for a flat panel detector that work efficiency of position adjustment of a flat panel detector can improved.

First Embodiment

Hereinafter, embodiments will be described by referring to the accompanying drawings.

First, the position adjustment device for a flat panel detector according to the first embodiment will be described by referring to FIG. 1 to FIG. 6.

Figure 1:
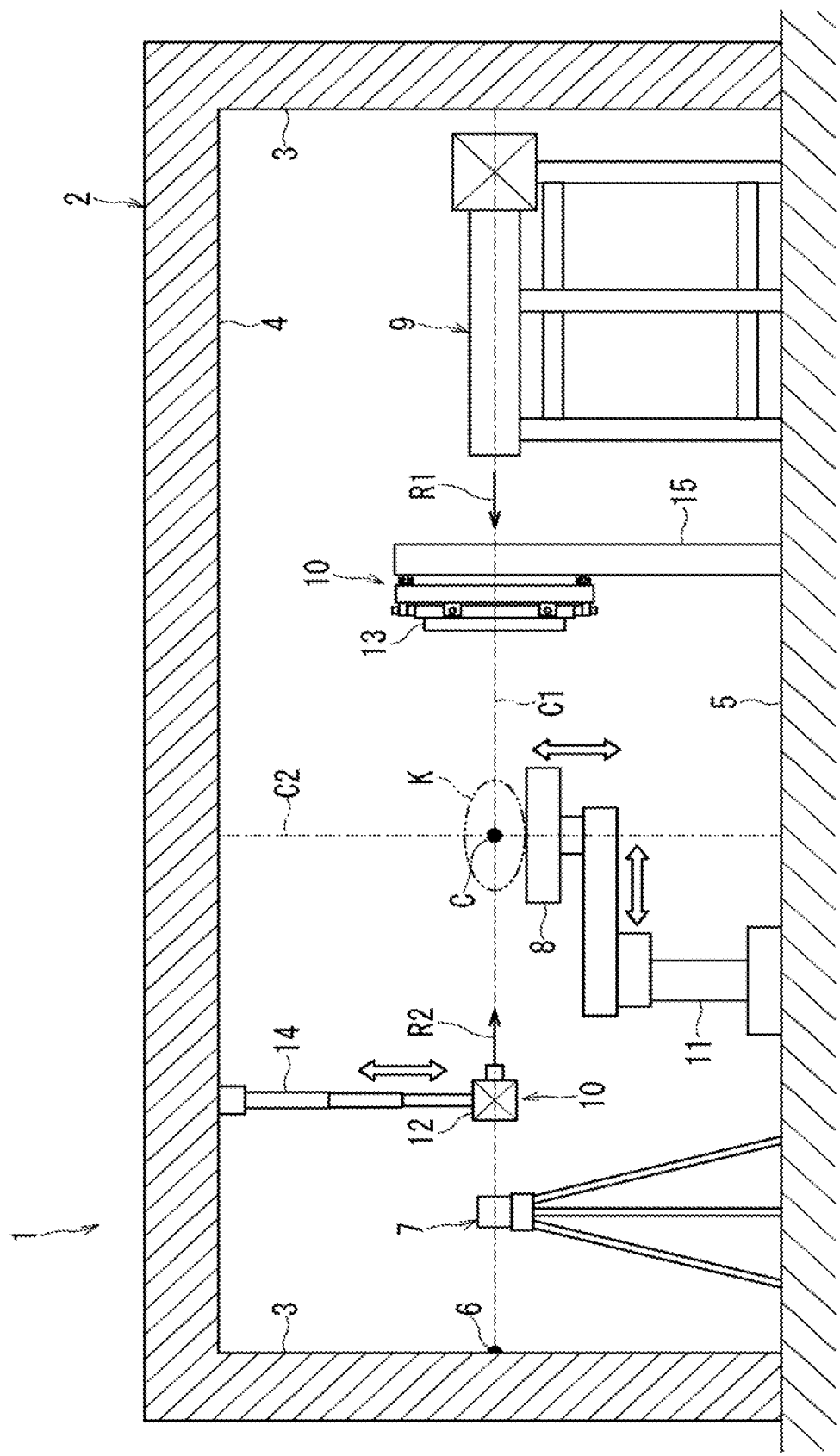
FIG. 1 is a side cross-sectional view of a treatment room in which a radiotherapy apparatus is installed.
Figure 3:
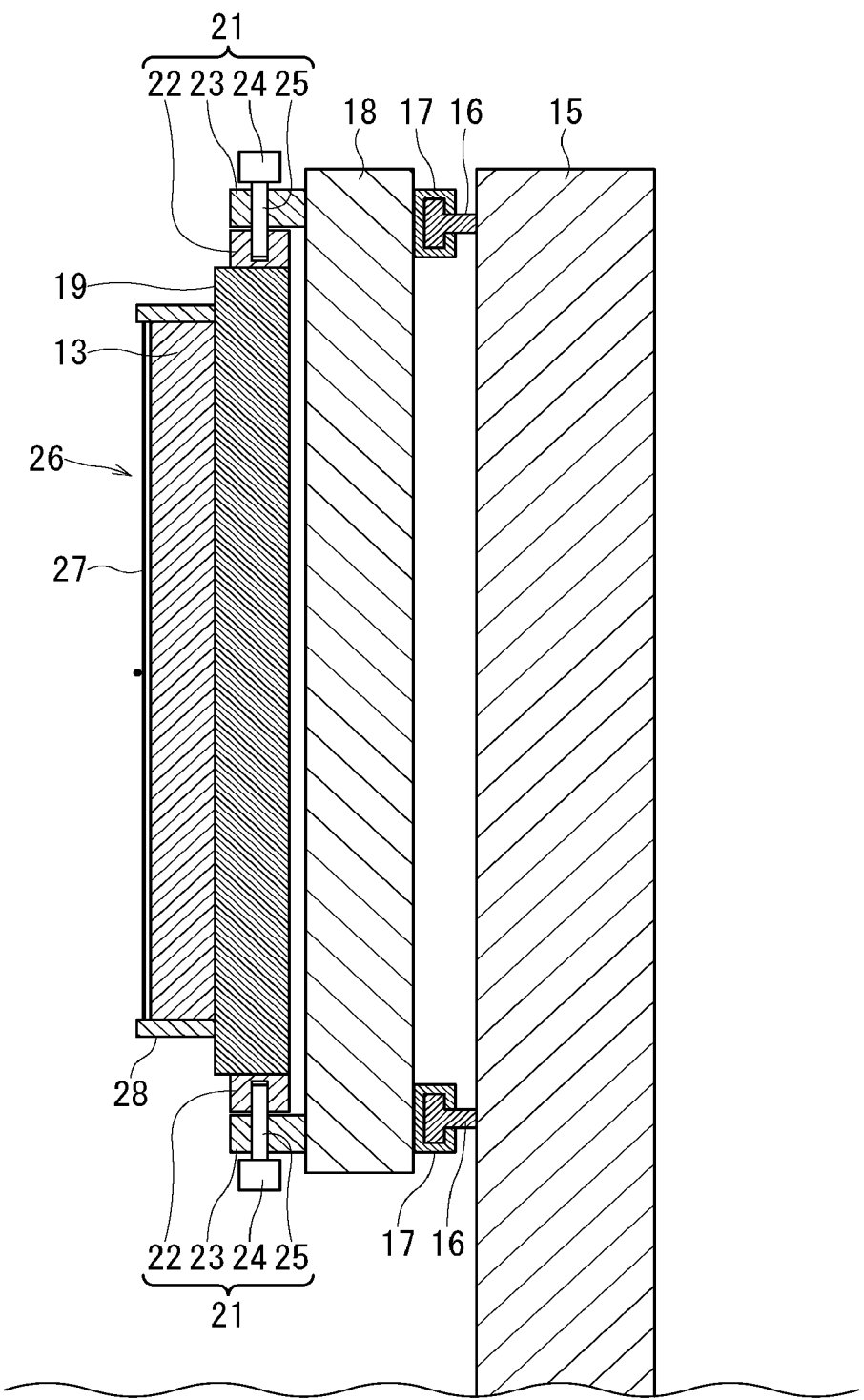
FIG. 3 is a side cross-sectional view illustrating the position adjustment device according to the first embodiment.

In the following description, it is assumed that the left side of the sheet of each of FIG. 1 and FIG. 3 is the front side (i.e., anterior side) of the flat panel detector and the position adjustment device.

The reference sign 1 in FIG. 1 denotes a radiotherapy apparatus. This radiotherapy apparatus 1 is installed in a treatment room 2.

The radiotherapy apparatus 1 is used for treatment in which a lesion area such as a tumor generated inside the body of a patient K as an object is irradiated with therapeutic radioactive rays. X-rays, gamma rays, electron beams, proton beams, neutron beams, and heavy particle beams are used for the therapeutic radioactive rays. Note that the treatment room 2 is a room surrounded by concrete walls 3, a ceiling 4 and a floor 5 that block radioactive rays.

In the treatment room 2, an isocenter C is set as the position where the therapeutic radioactive rays are concentrated most. On the walls 3 of the treatment room 2, reference marks (reference points) 6 are provided as the references for setting the isocenter C. The reference marks 6 are provided at plural positions on the four sides of the walls 3.

By measuring the respective positions of at least three reference marks 6 with the use of an optical device 7, the position of the isocenter C can be specified. Further, by measuring the respective positions of the reference marks 6 with the use of the optical device 7, it is possible to specify the transverse axis C1 and the longitudinal axis C1 of the isocenter C. In the present embodiment, the transverse axis C1 of the isocenter C forms a horizontal axis, and the longitudinal axis C1 of the isocenter C forms a vertical axis. The three-dimensional reference coordinate system of the treatment room 2 is determined by the transverse axis C1 and the longitudinal axis C1 of the isocenter C.

The optical device 7 of the present embodiment is a device capable of optically measuring a position, distance or angle. For instance, the optical device 7 is a light wave range finder (i.e., electro-optical distance meter), a transit, an auto level, a total station, or a laser tracker. In other words, the optical device 7 includes a device that can perform measurement using the naked eye of an operator and another device that can perform measurement using a laser beam. Further, the optical device 7 may be a device that measures two-dimensional positional relationship or a device that measures three-dimensional positional relationship.

When radiotherapy is performed, radioactive rays of sufficient power must be accurately radiated onto the position of the lesion area of the patient K. Further, it is necessary to suppress the exposure of normal tissues in the vicinity of the lesion area. For this reason, the patient K is imaged in order to generate the X-ray image depicting the lesion area immediately before the treatment and then confirm that the lesion area of the patient K is positioned at the isocenter C, and thereafter, irradiation of therapeutic radioactive rays is started.

The radiotherapy apparatus 1 includes a treatment table 8 on which the patient K is placed, a radiation irradiation apparatus 9 configured to irradiate the patient K with therapeutic radioactive rays, and an X-ray imaging apparatus 10 configured to irradiate the patient K with X-rays for generating an X-ray image immediately before the treatment.

During installation or maintenance of various devices, the optical device 7 is brought into the treatment room 2. Afterward, an operator measures the respective positions of the various devices and the respective positions of the reference marks 6 provided on the walls 3 by using the optical device 7. The worker compares the respective positions of the various devices with the position of the isocenter C acquired on the basis of the reference marks 6, and adjusts the position(s) of the device(s) when there is a positional deviation in at least one of the various devices.

The treatment table 8 is supported by a movable arm 11 installed on the floor 5. By operating the movable arm 11, the treatment table 8 is moved in the horizontal direction and in the vertical direction with the patient K placed thereon. Before start of the treatment, the lesion area of the patient K is positioned at the isocenter C by moving the treatment table 8 while the position of the lesion area of the patient K is checked by using the X-ray image.

The irradiation direction R1 of the therapeutic radioactive rays outputted from the radiation irradiation device 9 is oriented to the isocenter C. In other words, the therapeutic radioactive rays radiated from the radiation irradiation apparatus 9 pass through the isocenter C. In the present embodiment, the irradiation direction R1 of the therapeutic radioactive rays coincides with the transverse axis C1 of the isocenter C.

The X-ray imaging apparatus 10 includes an X-ray irradiator (i.e., X-ray tube) configured to radiate X-rays for X-ray imaging and a flat panel detector (FPD) 13 configured to generate an X-ray image by using X-rays radiated from the X-ray irradiator 12.

The X-ray irradiator 12 is suspended by an elevating/lowering arm 14 installed on the ceiling 4. By working the elevating/lowering arm 14, the X-ray irradiator 12 is lowered to the imaging position at the time of X-ray imaging. Further, at the time of starting radiotherapy, the X-ray irradiator 12 is raised to the retreat position.

In addition, the irradiation direction R2 of the X-rays radiated from the X-ray irradiator 12 at the imaging position is oriented to the isocenter C. In other words, the X-rays radiated from the X-ray irradiator 12 pass through the isocenter C. In the present embodiment, the irradiation direction R2 of X-rays coincides with the transverse axis C1 of the isocenter C. Further, the flat panel detector 13 is disposed ahead of (i.e., on the extended line of) the X-ray irradiation direction R2.

Figure 4:
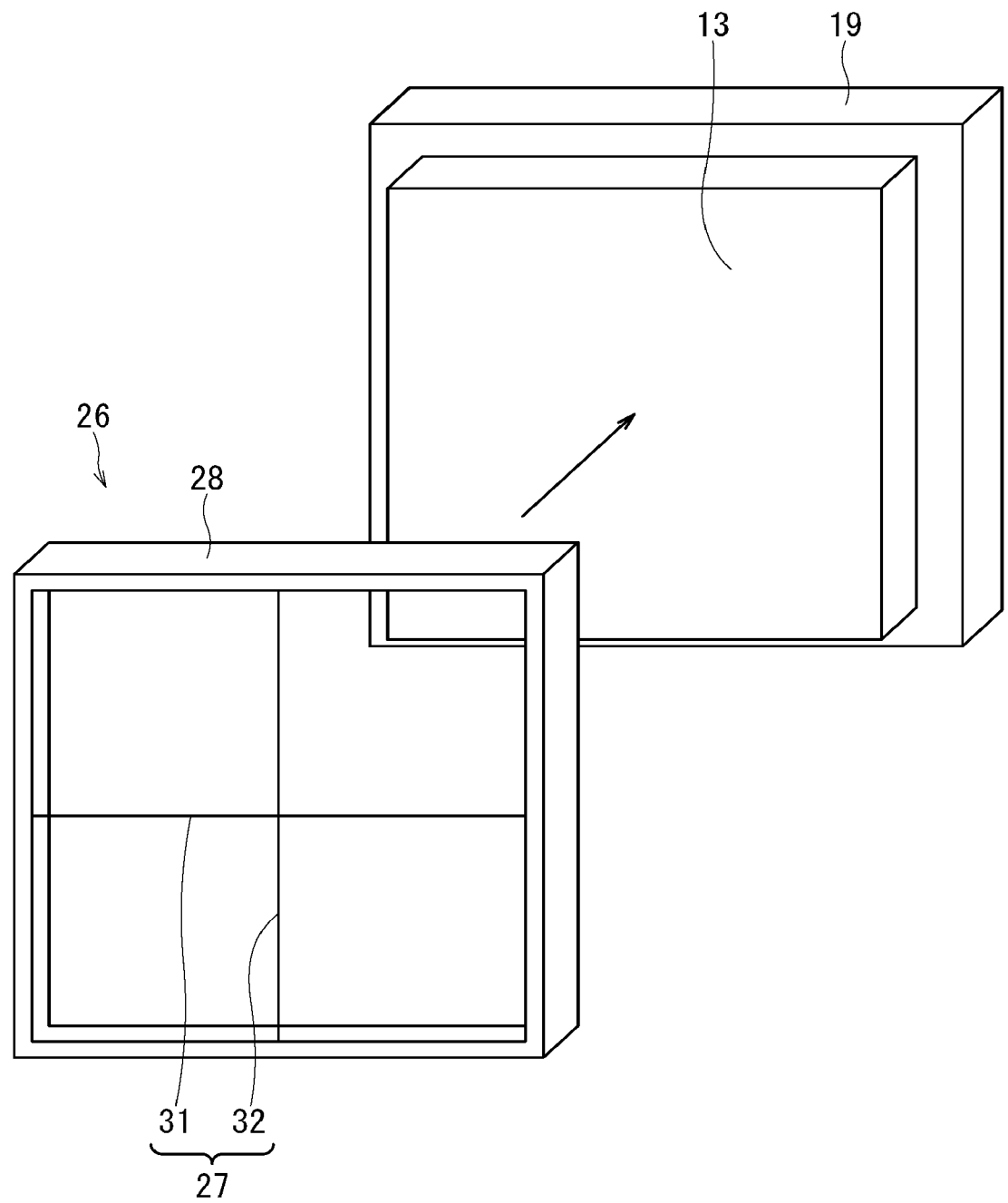
FIG. 4 is a perspective view illustrating the position adjustment device according to the first embodiment.

The flat panel detector 13 is an imaging device used for computer X-ray imaging. The flat panel detector 13 is an electronic device in the form of a flat plate (FIG. 4). In the present embodiment, the flat panel detector 13 has a quadrangular shape when viewed from the front (FIG. 2). By radiating X-rays onto the flat surface of the flat panel detector 13, an X-ray image is generated.

The flat panel detector 13 includes scintillators that are provided for the respective pixels and convert the incident X-rays into light. The light of each scintillator is converted into an electric signal by the photodiode constituting each pixel. The converted electric signals of the respective scintillators are read through the thin film transistor switches. Further, electric signals are processed by the analog/digital conversion elements and the low noise amplification circuit such that an X-ray image is generated.

As shown in FIG. 1, the flat panel detector 13 is supported by a plate-shaped base 15 erected from the floor 5. The flat panel detector 13 is disposed on the front side of the base 15.

As shown in FIG. 3, two rows of upper and lower rails 16 extending horizontally are fixed to the front side of the base 15. Two slides 17 are supported by the respective rails 16. The slides 17 are fixed to the back surface of the support portion 18. In other words, the support portion 18 is supported on the rails 16 so as to be movable in the horizontal direction. Further, on the front side of the support portion 18, a moving portion 19 movable with respect to the support portion 18 is provided. The flat panel detector 13 is fixed to the front side of the moving portion 19.

The flat panel detector 13 can move in the horizontal direction between the imaging position (FIG. 2A) at the time of X-ray imaging and the retreat position (FIG. 2B) at the time of radiotherapy.

In the base 15, an opening 20 is provided at the position corresponding to the radiation irradiation apparatus 9. When the flat panel detector 13 is at the retreat position, therapeutic radioactive rays can be radiated from the radiation irradiation apparatus 9 toward the isocenter C. When the flat panel detector 13 is at the imaging position, X-rays radiated from the X-ray irradiator 12 are made incident on the flat panel detector 13.

Further, between the moving portion 19 and the support portion 18, position adjusters 21 are provided as position adjustment units for an operator to manually adjust the position of the flat panel detector 13.

Each of the position adjusters 21 includes a first member 22 fixed to the moving portion 19 to which the flat panel detector 13 is fixed, a second member 23 fixed to the support portion 18, and an operation unit 24 for adjusting the distance between the first member 22 and the second member 23.

In the present embodiment, each position adjuster 21 is provided between the flat panel detector 13 and its support portion 18. Further, the first member 22 is fixed to the flat panel detector 13 via the moving portion 19. That is, the first member 22 is a member on the flat panel detector side of each position adjuster 21. Additionally, the second member 23 is fixed to the support portion 18. In other words, the second member 23 is a member on the support portion side of each position adjuster 21. Further, a gap for distance adjustment is provided between the first member 22 and the second member 23.

For each of the position adjusters 21, a female screw hole is formed in the first member 22 and the second member 23, and a male screws 25 screwed into the female screw hole is provided. The operator can turn the male screw 25 by manually turning the operation unit 24. By the rotation of the male screw 25, the distance between the first member 22 and the second member 23 can be adjusted.

Figure 2A:
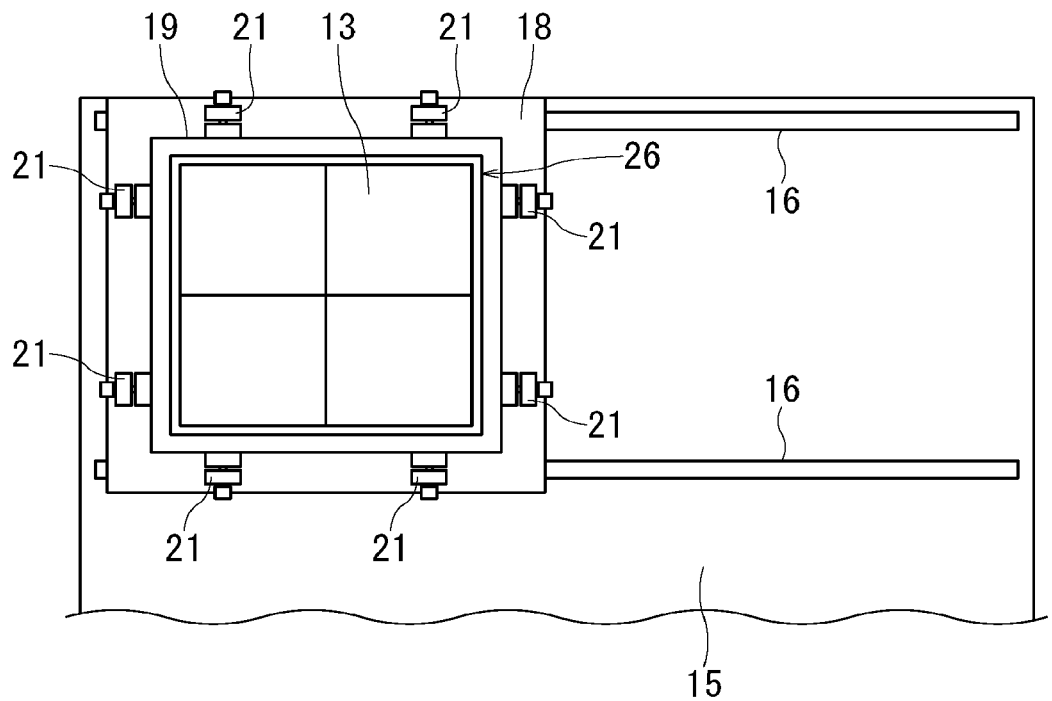
FIG. 2A is a front view of a flat panel detector illustrating an imaging position of the flat panel detector at the time of X-ray imaging.
Figure 2B:
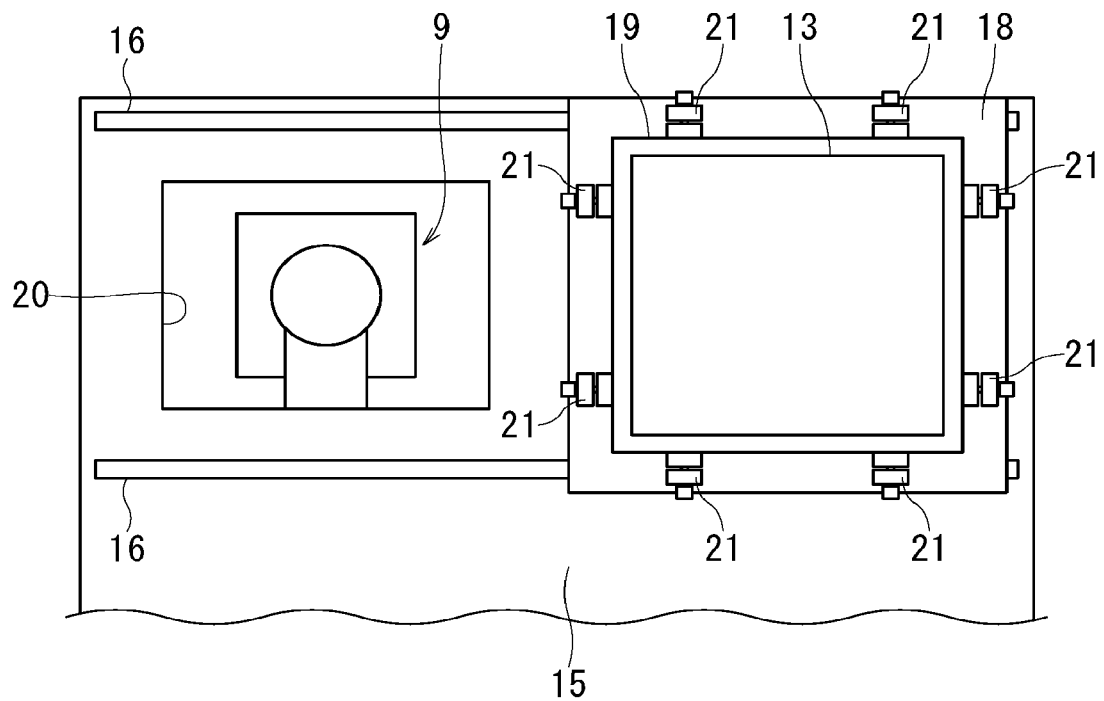
FIG. 2B is a front view of the flat panel detector illustrating a retreat position of the flat panel detector when radiotherapy is performed.

As shown in FIG. 2A, two position adjusters 21 are provided for each of the four sides of the flat panel detector 13. An operator can perform fine position adjustment of the flat panel detector 13 in the transverse (i.e., X-axis) direction or the longitudinal (i.e., Y-axis) direction by operating the operation unit 24 of each of the position adjusters 21.

As shown in FIG. 3 and FIG. 4, a position adjustment device 26 used for fine positional adjustment is detachably attached to the flat panel detector 13. The position adjustment device 26 includes a guide 27 contacting the surface of the flat panel detector 13 and a fixing member 28 that is fixed to the periphery of the flat panel detector 13. The guide 27 includes various forms such as a marker, a marking, an index point to be positionally detected or measured, and a structure functioning as a positional mark or a positional indicator.

The guide 27 is composed of wires 31 and 32. The wire 31 extends so as to correspond to the transverse direction (i.e., X-axis direction) of the flat panel detector 13, and the wire 32 extends so as to correspond to the longitudinal direction (i.e., Y-axis direction) of the flat panel detector 13. The end portions of the two wires 31 and 32 are fixed to the center of each of the four sides of the frame-shaped fixing member 28. The two wires 31 and 32 are arranged in a cross shape. The intersection angle between the wires 31 and 32 is 90 degrees.

Further, the wires 31 and 32 are provided such that the intersection point of the wires 31 and 32 positionally corresponds to the substantially central position of the flat panel detector 13. Each of these wires 31 and 32 is formed in such a straight line that the two axes of two-dimensional coordinates corresponding to the surface of the flat panel detector 13 can be measured by the optical device 7.

In addition, the wires 31 and 32 are made of metal. Thus, when X-rays are radiated in the state where the wires 31 and 32 are arranged on the surface of the flat panel detector 13, the wires 31 and 32 are depicted in the X-ray image. By using these wires 31 and 32, it is possible to easily form the guide 27 that can be depicted in an X-ray image and can be measured by the optical device 7. In other words, the position of the guide 27 can be specified by the X-ray image. It should be noted that the fixing member 28 may be made of metal depicted in an X-ray image or may be made of synthetic resin that is not depicted in an X-ray image.

The fixing member 28 is fixed to the flat panel detector 13 or the moving portion 19. In addition, the respective first members 22 of the position adjusters 21 are fixed to the four sides of the moving portion 19. In other words, the fixing member 28 is fixed to the first member 22 on the flat panel detector side of each position adjuster 21.

As shown in FIG. 2A, the position adjustment device 26 is attached to the flat panel detector 13 at the time of installation or maintenance of various devices. By radiating X-rays from the X-ray irradiator 12 to the flat panel detector 13, X-ray imaging is performed to generate an X-ray image for position adjustment. On the basis of this X-ray image, an operator checks whether the image center of the flat panel detector 13 is accurately arranged at the position corresponding to the isocenter C or not. When the image center of the flat panel detector 13 is not accurately arranged at the position corresponding to the isocenter C, the operator refers to the guide 27 of the position adjustment device 26 and adjusts the position of the flat panel detector 13.

Figure 5:
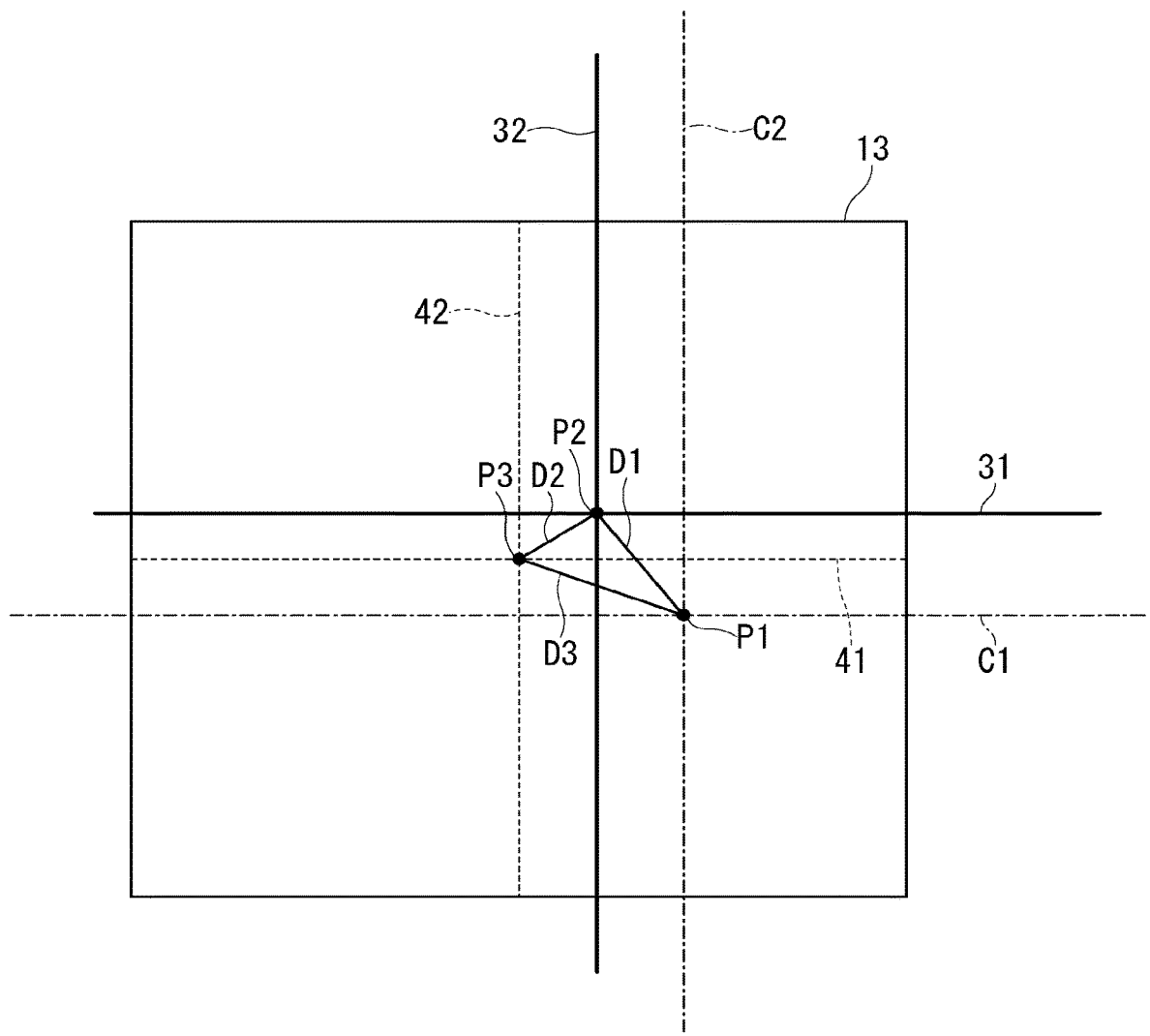
FIG. 5 is a conceptual diagram illustrating the position adjustment method with the use of the position adjustment device of the first embodiment.

Next, a description will be given of an embodiment of position adjustment with the use of the flat panel detector 13 in detail. FIG. 5 is a conceptual diagram illustrating the state in which the flat panel detector 13 is viewed from the front.

As to reference signs in FIG. 5, P1 is defined as the first position that corresponds to the isocenter C and is the intersection point of the transverse axis C1 (e.g., horizontal axis) and the longitudinal axis C1 (e.g., vertical axis) of the isocenter C.

P2 is defined as the second position where the two wires 31 and 32 of the guide 27 intersect.

P3 is defined as the third position that is the intersection of the central transverse axis 41 and the central longitudinal axis 42 of the flat panel detector 13 and corresponds to the image center of the X-ray image.

Further, the first difference between the first position P1 and the second position P2 is defined as D1. The second difference between the second position P2 and the third position P3 is defined as D2. The third difference between the first position P1 and the third position P3 is defined as D3. The term "difference" in the present embodiment means a difference in two-dimensional coordinate. In addition, the term "difference" includes at least one of the direction of the positional deviation and the distance of the positional deviation.

Since the isocenter C and the guide 27 can be measured by the optical device 7, the first difference D1 can be specified by the optical device 7. Additionally, since the guide 27 composed of the wires 31 and 32 appears on the X-ray image, the second difference D2 can be specified by the X-ray image. Further, by specifying the first difference and the second difference, the third difference D3 can be specified.

By specifying the third difference D3, it is possible to grasp the positional deviation amount between the first position P1 corresponding to the isocenter C and the third position P3 that is the image center of the flat panel detector 13. Accordingly, an operator measures the guide 27 by using the optical device 7, and operates the operation units 24 of the respective position adjusters 21 so as to move the flat panel detector 13 while checking the second position P2. At this time, the moving direction and moving distance of the second position P2 are adjusted so as to match the direction and the distance, each of which corresponds to the third difference D3.

For instance, in FIG. 5, the third position P3 is displaced to the upper left of the first position P1. Thus, the operator moves the second position P2 to the lower right. At this time, the movement direction of the second position P2 is made to correspond to the inclination of the third difference D3, and the movement distance of the second position P2 is made to correspond to the length of the third difference D3. As described above, the operator operates the position adjusters 21 so as to move the flat panel detector 13 while checking the position of the guide 27 by using the optical device 7, in such a manner that the second position P2 is moved.

At the stage when the first difference D1 is specified, the operator may move the flat panel detector 13 by manipulating the position adjusters 21 such that the second position P2 coincides with the first position P1. In other words, the first difference D1 may be set to zero in advance. By previously setting the first difference D1 to zero, it is possible to save time and effort of calculating the third difference D3 on the basis of the first difference and the second difference.

Since each of the two wires 31 and 32 of the guide 27 is formed in such a straight line that the two axes of the two-dimensional coordinates corresponding to the surface of the flat panel detector 13 can be measured by using the optical device 7, the movement amount of the flat panel detector 13 in the X-axis direction and the Y-axis direction can be checked.

After completion of the position adjustment of the flat panel detector 13 with the use of the position adjusters 21, the position adjustment device 26 is detached from the flat panel detector 13.

Figure 6:
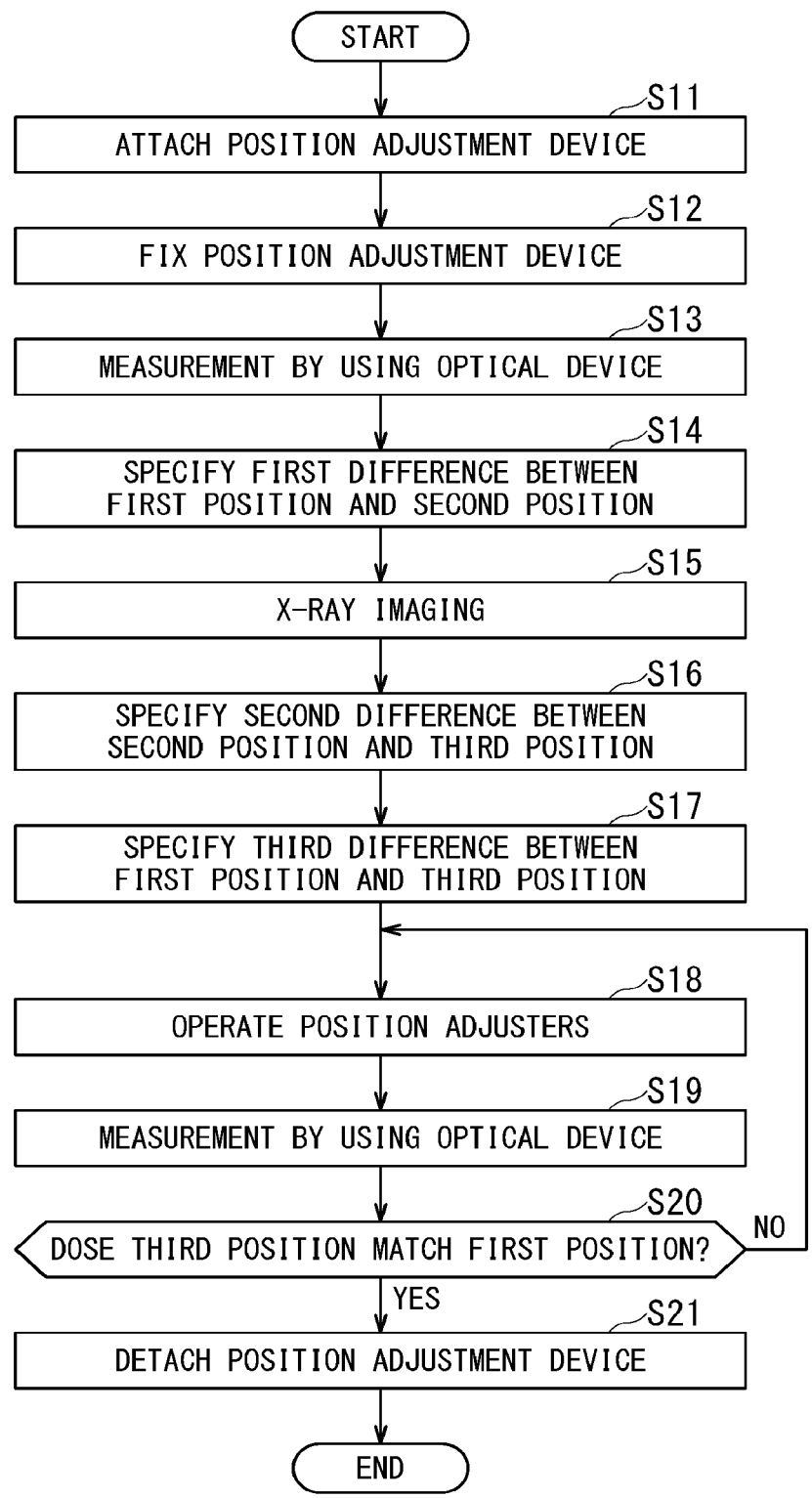
FIG. 6 is a flowchart illustrating the position adjustment method according to the first embodiment.

Next, the position adjustment method with the use of the position adjustment device 26 will be described by referring to the flowchart of FIG. 6.

First, in the step S11, the operator attaches the position adjustment device 26 to the flat panel detector 13. At this time, the guide 27 is provided on the front surface side of the flat panel detector 13.

In the next step S12, the operator fixes the fixing member 28 of the position adjustment device 26 to the flat panel detector 13 or the moving portion 19. Here, the fixing member 28 may be screwed to the flat panel detector 13 or the moving portion 19, or may be fixed by using a predetermined clamp.

In the next step S13, the operator measures the first position P1 corresponding to the isocenter C and the second position P2 indicated by the guide 27 by using the optical device 7.

In the next step S14, the operator specifies the first difference D1 between the first position P1 and the second position P2, on the basis of the first position P1 and the second position P2 measured by the optical device 7.

In the next step S15, the operator operates the X-ray imaging apparatus 10 to radiate X-rays from the X-ray irradiator 12 in the irradiation direction R2 passing through the isocenter C. By making the X-rays incident on the flat panel detector 13, X-ray imaging is performed, and thereby an X-ray image depicting the wires 31 and 32 of the guide 27 is generated. The operator measures the second position P2 and the third position P3 from this X-ray image.

In the next step S16, the operator specifies the second difference D2 between the second position P2 and the third position P3, on the basis of the second position P2 and the third position P3 measured by the X-ray image.

In the next step S17, the operator specifies the third difference D3 between the first position P1 and the third position P3 on the basis of the first difference D1 and the second difference D2.

In the next step S18, the operator operates the position adjusters 21 so as to move the flat panel detector 13 in such a direction that the third difference D3 becomes zero. As the flat panel detector 13 moves in this manner, the guide 27 is also moved.

In this manner, the operator can easily perform the position adjustment of the flat panel detector 13 by checking the position of the guide 27 with the use of the optical device 7 and operating the operation unit 24. Since the guide 27 is interlocked with (i.e., moved in conjunction with) the first member 22 by operating the operation unit 24, it is possible to easily adjust the position of the flat panel detector 13.

Further, since the guide 27 is fixed to the flat panel detector 13, the flat panel detector 13 and the guide 27 are moved together and thus adjustment using the optical device 7 becomes easy.

In the next step S19, the operator measures the second position P2 indicated by the guide 27 by using the optical device 7.

In the next step S20, the operator determines whether the moving direction and the moving distance of the second position P2 match the direction and the distance corresponding to the third difference D3 or not, i.e., whether the third position P3 being the image center of the flat panel detector 13 matches the first position P1 that is the target position corresponding to the isocenter C or not.

When the third position P3 does not match the first position P1, the processing returns to the above-described step S18 (corresponding to NO in the step S20). Conversely, when the third position P3 matches the first position P1, the processing proceeds to the step S21 (corresponding to YES in the step S20).

In the next step S21, the operator unlocks the fixing member 28, detaches the position adjustment device 26 from the flat panel detector 13, and completes the work.

In this manner, the image center of the flat panel detector 13 can be positioned at the isocenter C. In the present embodiment, when the position adjusters 21 are operated to move the flat panel detector 13, only the measurement using the optical device 7 is sufficient. In other words, it is not necessary to perform X-ray imaging, and thus work can be completed in a short period of time. As described above, it is possible to shorten the inspection adjustment period of the radiotherapy apparatus 1. Further, the reliability of various devices can be maintained.

In the present embodiment, since the guide 27 is in contact with the surface of the flat panel detector 13, the distance from the flat panel detector 13 to the guide 27 is shorter than the distance from the flat panel detector 13 to the X-ray irradiator 12. Thus, the accuracy of the position adjustment of the flat panel detector 13 can be improved.

Incidentally, the processing of the steps S13 to S20 may be repeated until the flat panel detector 13 is accurately moved to the target position.

Although X-rays radiated from the X-ray irradiator 12 pass through the isocenter C in the first embodiment, it is not necessarily required that the X-rays radiated from the X-ray irradiator 12 pass through the isocenter C at the time of adjusting the position of the flat panel detector 13. Also in this case, since the guide 27 is close to the surface of the flat panel detector 13, the accuracy of the position adjustment is improved.

After the position adjustment of the flat panel detector 13 is completed, by installing a calibration phantom at the isocenter C and imaging this calibration phantom to generate its X-ray image, the position adjustment of the X-ray irradiator 12 may be performed on the basis of this X-ray image such that X-rays pass through the isocenter C.

Although a description has been given of the adjustment in the X-axis and Y-axis directions of the flat panel detector 13 in the present embodiment, there is a separate adjustment mechanism for adjusting the distance direction from the isocenter C and the surface accuracy (X-Y plane) of the flat panel detector 13, and the adjustment in the X-Y plane described in the present embodiment is performed after adjusting the distance direction from the isocenter C and the surface accuracy of the flat panel detector 13.

Second Embodiment

Next, the position adjustment device 26A for the flat panel detector according to the second embodiment will be described by referring to FIG. 7 and FIG. 8. Note that the same reference signs are assigned to the same components as the above-described embodiment in each figure, and duplicate description is omitted.

Figure 7:
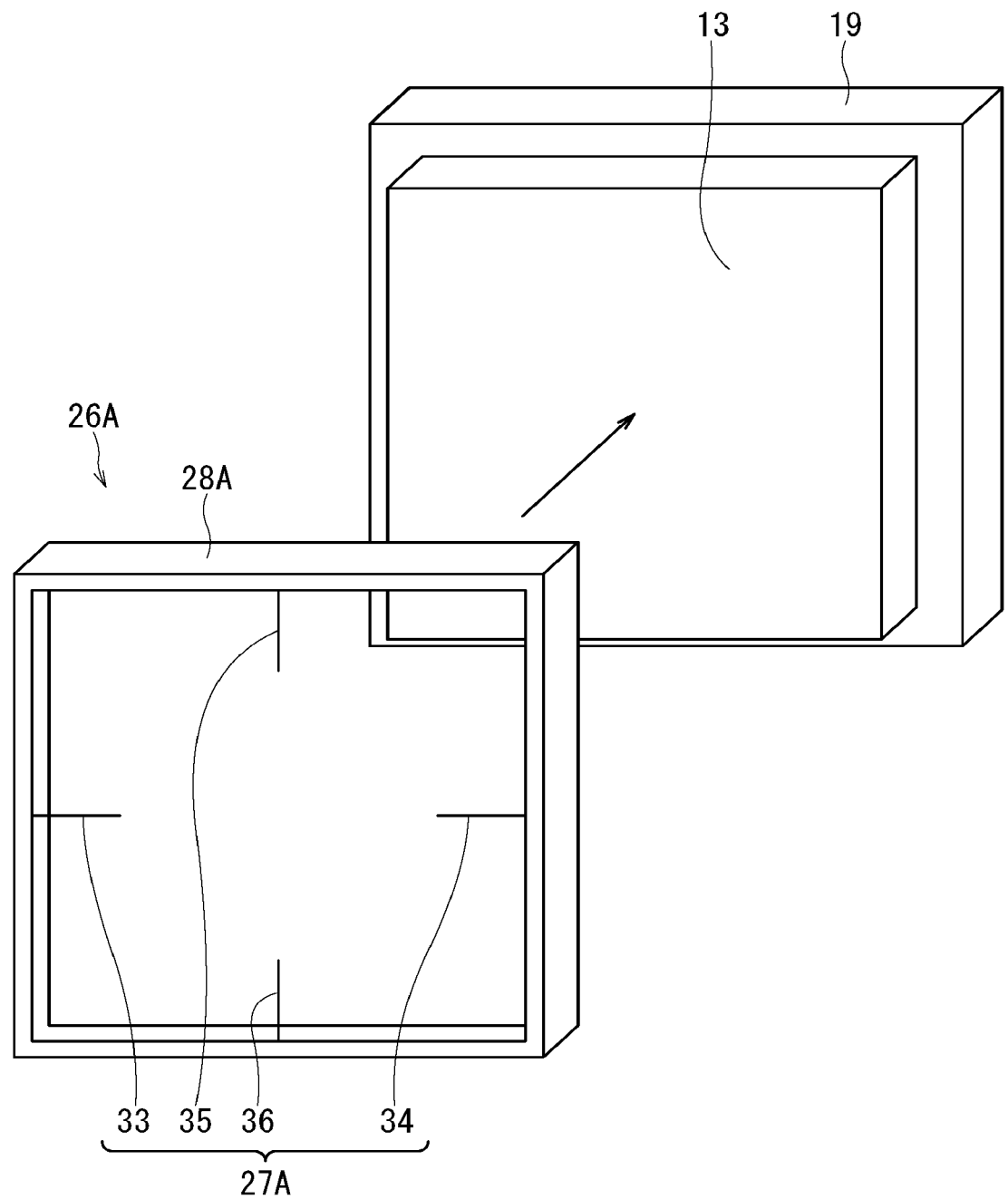
FIG. 7 is a perspective view illustrating the position adjustment device according to the second embodiment.

As shown in FIG. 7, the position adjustment device 26A according to the second embodiment is attached to the flat panel detector 13. The position adjustment device 26A, includes a guide 27A, being in contact with the surface of the flat panel detector 13 and a fixing member 28A that is fixed to the periphery of the flat panel detector 13.

The guide 27A is composed of four wires 33, 34, 35, and 36 extending from the center of each of the four sides of the frame-shaped fixing member 28A toward the center of the frame. Each of these wires 33, 34, 35, and 36 is formed in such a linear shape that the two axes of the two-dimensional coordinates corresponding to the surface of the flat panel detector 13 can be measured by using the optical device 7.

Figure 8:
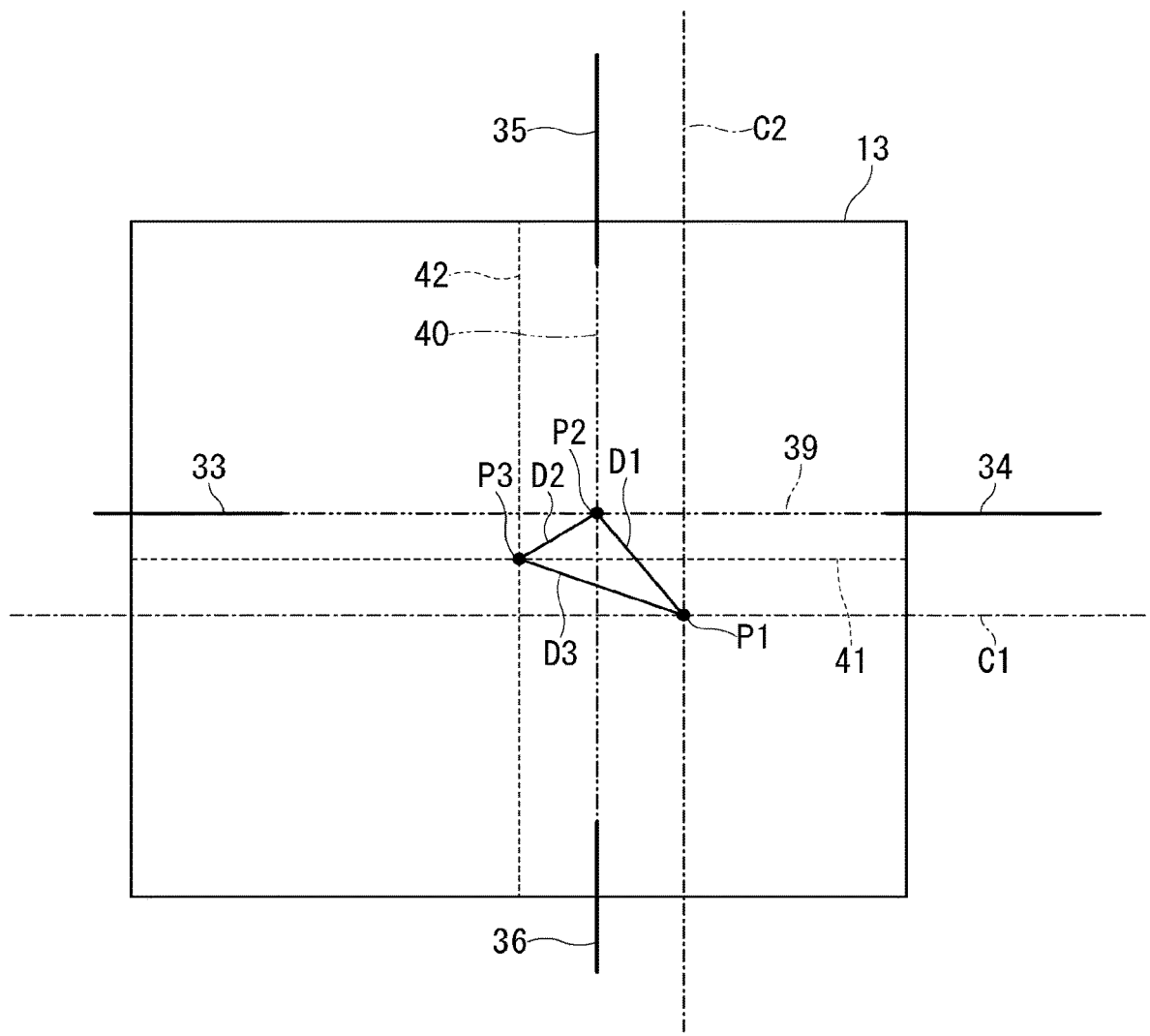
FIG. 8 is a conceptual diagram illustrating the position adjustment method with the use of the position adjustment device according to the second embodiment.

As shown in FIG. 8, the intersection angle between the virtual lines 39 and 40 obtained by extending the respective wires 33, 34, 35, and 36 is 90 degrees. The virtual lines 39 and 40 are provided such that the intersection point of the virtual lines 39 and 40 corresponds to the substantially central position of the flat panel detector 13.

The virtual line 39 of the right and left two wires 33 and 34 extending and corresponding to the transverse direction (X-axis) of the flat panel detector 13 is provided at the same position in the longitudinal direction. In other words, the X-axis of the two-dimensional coordinates can be specified by the right and left two wires 33 and 34.

Further, the virtual line 40 of the upper and lower two wires 35 and 36 extending and corresponding to the longitudinal direction (Y-axis) of the flat panel detector 13 is provided at the same position in the transverse direction. In other words, the Y-axis of the two-dimensional coordinates can be specified by the upper and lower two wires 35 and 36.

As to the reference signs in FIG. 8, P2 is defined as the second position at which the virtual lines 39 and 40 of the four wires 33, 34, 35, and 36 of the guide 27A intersect. The other reference signs including the first position P1, the third position P3, the first difference D1, the second difference D2, and the third difference D3 are the same as those of the first embodiment described above.

Since the four wires 33, 34, 35, and 36 of the guide 27A and the isocenter C can be measured by the optical device 7, the first difference D1 can be specified by the optical device 7 on the basis of the virtual lines 39 and 40 of the wires 33, 34, 35, and 36. Further, since the four wires 33, 34, 35, and 36 of the guide 27A appear in the X-ray image, the second difference D2 can be specified by the X-ray image on the basis of the virtual lines 39 and 40 of the wires 33, 34, 35, and 36. By specifying the first difference D1 and the second difference D2, the third difference D3 can be specified.

By specifying the third difference D3, it is possible to calculate the positional deviation amount between the first position P1 corresponding to the isocenter C and the third position P3 that is the image center of the flat panel detector 13. Thus, the operator measures the guide 27A by using the optical device 7 and operates the operation unit 24 of the position adjusters 21 as the position adjustment unit so as to move the flat panel detector 13 while checking the second position P2. At this time, the moving direction and moving distance of the second position P2 are adjusted so as to match the direction and the distance that correspond to the third difference D3.

By measuring the plural wires 33, 34, 35, and 36 with the use of the optical device 7, the axes of the two-dimensional coordinates corresponding to the surface of the flat panel detector 13 can be measured. In other words, by measuring the movement amount of the plural wires 33, 34, 35, and 36 with the use of the optical device 7, the movement amount of the flat panel detector 13 can be checked.

In the second embodiment, the plural wires 33, 34, 35, and 36 are plural markers depicted in the X-ray image. When the position adjustment device 26A is attached to the flat panel detector 13, the wires 33, 34, 35, and 36 are provided on the peripheral portion of the flat panel detector 13.

In this manner, since the plural wires 33, 34, 35, and 36 depicted in the X-ray image are not positioned at the image center of the flat panel detector 13, the wire 33, 34, 35, and 36 do not become an obstacle to imaging when the patient K as the object is imaged for generating the X-ray image. In other words, according to the second embodiment, after the position adjusters 21 adjust the position of the flat panel detector 13, radiotherapy can be performed by radiating radioactive rays without detaching the position adjustment device 26A from the flat panel detector 13.

Third Embodiment

Next, the position adjustment device 26B for the flat panel detector according to the third embodiment will be described by referring to FIG. 9 and FIG. 10. Note that the same reference signs are assigned to the same components as the above-described embodiments in each figure, and duplicate description is omitted. In the following description, it is assumed that the left side of the sheet of FIG. 9 is the front side (i.e., anterior side) of the flat panel detector 13 and the position adjustment device 26B.

Figure 9:
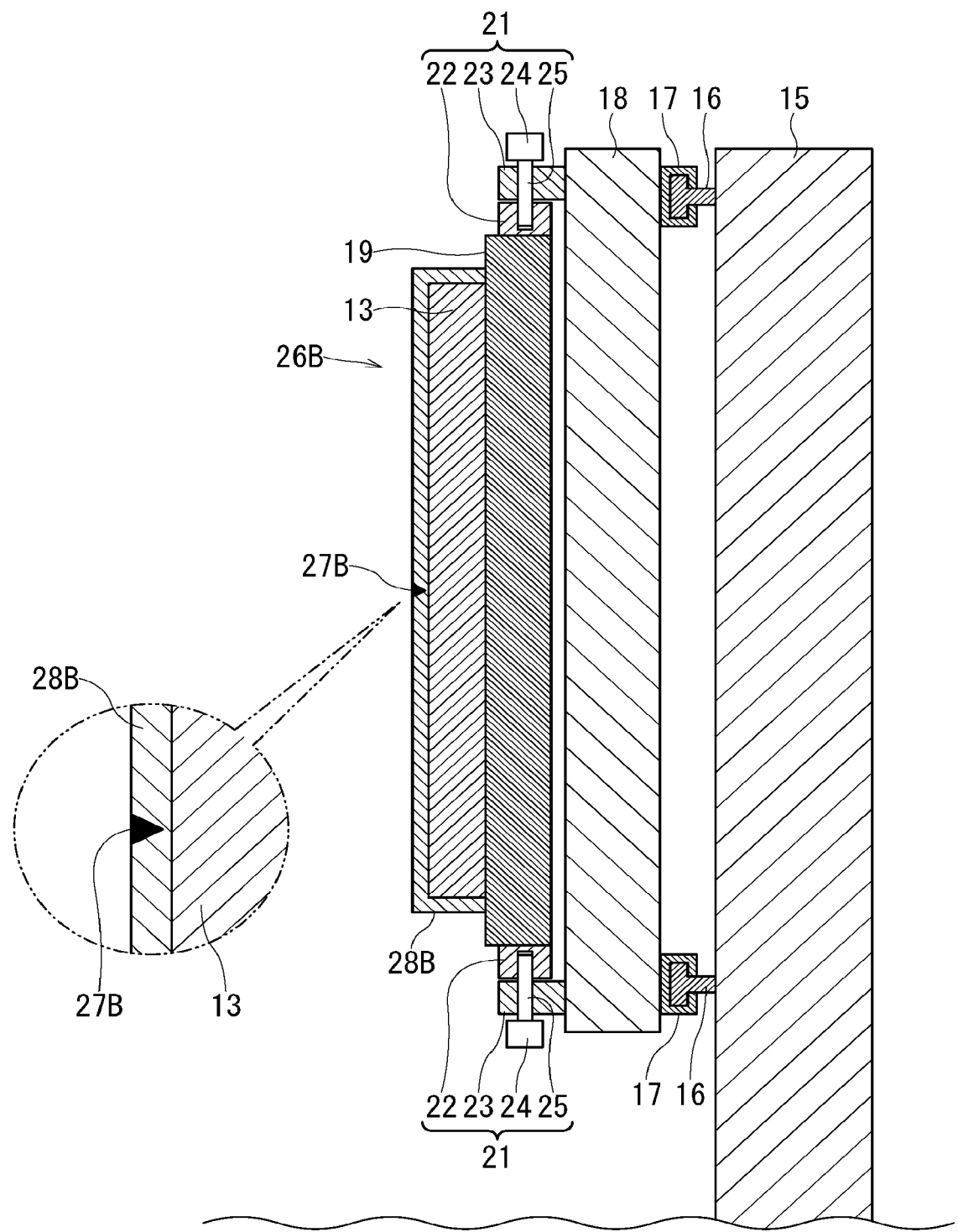
FIG. 9 is a side cross-sectional view illustrating the position adjustment device according to the third embodiment.
Figure 10:
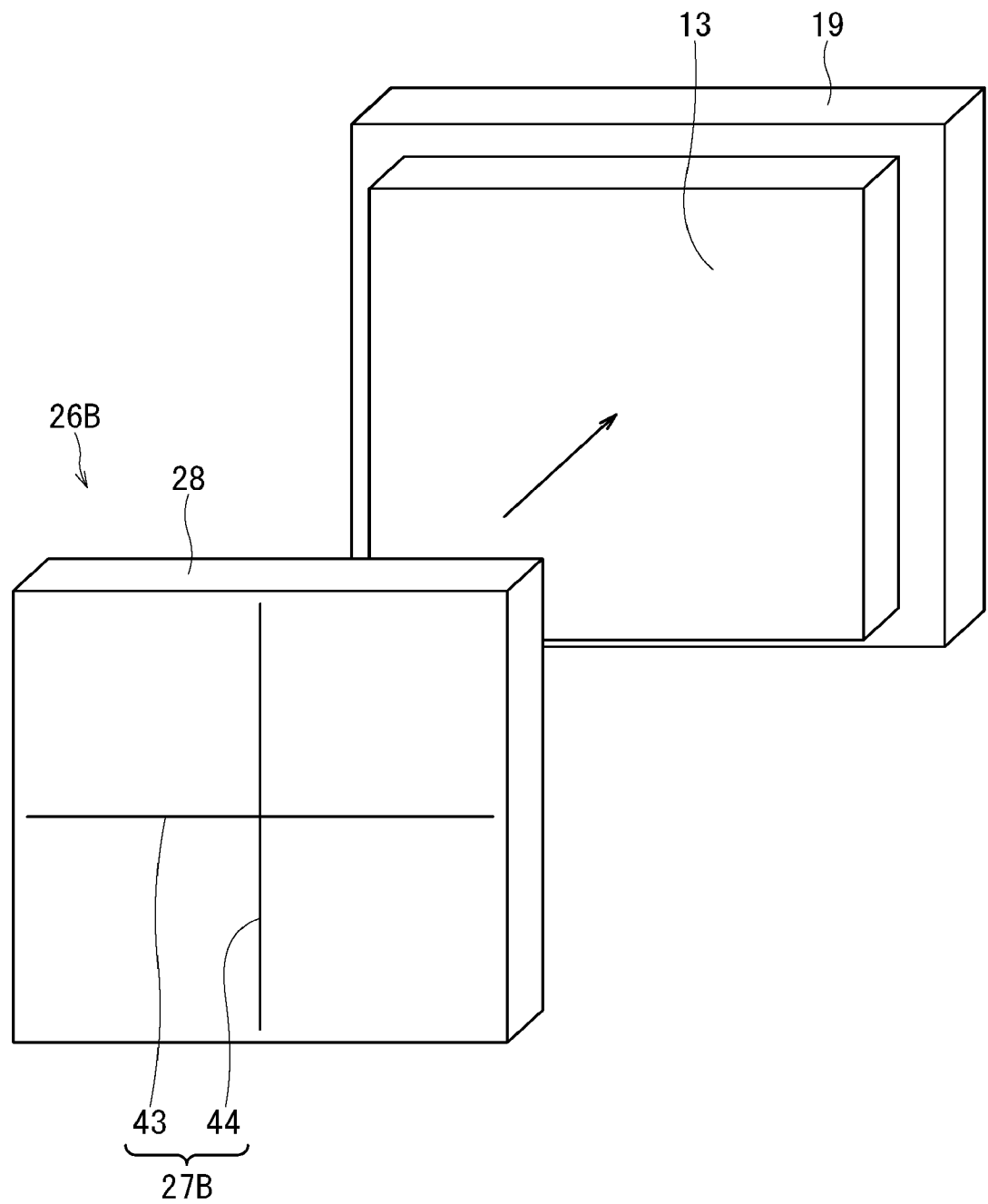
FIG. 10 is a perspective view illustrating the position adjustment device according to the third embodiment.

As shown in FIG. 9 and FIG. 10, the position adjustment device 26B according to the third embodiment has a substantially C-shape in a side cross-sectional view and is a box-shaped member opened on the back side. The position adjustment device 26B is configured to interdigitate with (i.e., fit into) the flat panel detector 13. The position adjustment device 26B includes a guide 27B provided on the front side and a fixing member 28B having a box shape to be fitted into the flat panel detector 13. The position adjustment device 26B is detachably attached to the flat panel detector 13.

The guide 27B is composed of lines 43 and 44. The line 43 extends so as to correspond to the transverse direction (i.e., X-axis) of the flat panel detector 13, and the line 44 extends so as to correspond to the longitudinal direction (i.e., Y-axis) of the flat panel detector 13. The two lines 43 and 44 are arranged in a cross shape.

In addition, the intersection angle between the lines 43 and 44 arranged in a cross shape is 90 degrees. Further, the lines 43 and 44 are provided such that the intersection point of the lines 43 and 44 corresponds to the substantially central position of the flat panel detector 13. Each of the lines 43 and 44 is formed in such a straight line that the two axes of the two-dimensional coordinates corresponding to the surface of the flat panel detector 13 can be measured by using the optical device 7.

The fixing member 28B is made of synthetic resin that is not depicted in an X-ray image. The four sides of the fixing member 28B are fixed to the flat panel detector 13 or the moving portion 19. Here, the fixing member 28B may be screwed or may be fixed by using a predetermined clamp. A latching piece to be latched by the flat panel detector 13 or the moving portion 19 may be provided on each of the four sides of the fixing member 28B.

As shown in the partially enlarged view of FIG. 9, in the front side of the fixing member 28B, a V-shaped groove is formed at the position corresponding to the guide 27B. Further, by filling this groove with resin containing a metal to be depicted in an X-ray image, the guide 27B is formed.

When X-rays are radiated under the state where the position adjustment device 26B is attached to the flat panel detector 13, the images of the lines 43 and 44 of the guide 27B are depicted in the X-ray image. In other words, the position P2 (FIG. 5) of the intersection point of the lines 43 and 44 of the guide 27B can be specified by the X-ray image.

The other positions including the first position P1, the third position P3, the first difference D1, the second difference D2, and the third difference D3 are the same as those of the first embodiment (FIG. 5). By specifying the third difference D3, the positional deviation amount between the first position P1 corresponding to the isocenter C and the third position P3 that is the image center of the flat panel detector 13 is grasped. Accordingly, an operator measures the guide 27B by using the optical device 7, and operates the operation units 24 of the respective position adjusters 21 as the position adjustment unit so as to move the flat panel detector 13 while checking the second position P2.

Thus, according to the third embodiment, it is possible to obtain the same function and the same effect as in the above-described first embodiment with a simple structure.

In the third embodiment, the flat panel detector 13 is attached before the position adjustment of the flat panel detector 13 with the use of the position adjusters 21. After the position adjustment of the flat panel detector 13 with the use of the position adjusters 21, the position adjustment device 26B is detached from the flat panel detector 13.

Fourth Embodiment

Next, the position adjustment device 26C for the flat panel detector according to the fourth embodiment will be described by referring to FIG. 11 and FIG. 12. Note that the same reference signs are assigned to the same components as the above-described embodiment in each figure, and duplicate description is omitted. In the following description, it is assumed that the left side of the sheet of FIG. 11 is the front side (i.e., anterior side) of the flat panel detector 13 and the position adjustment device 26C.

Figure 11:
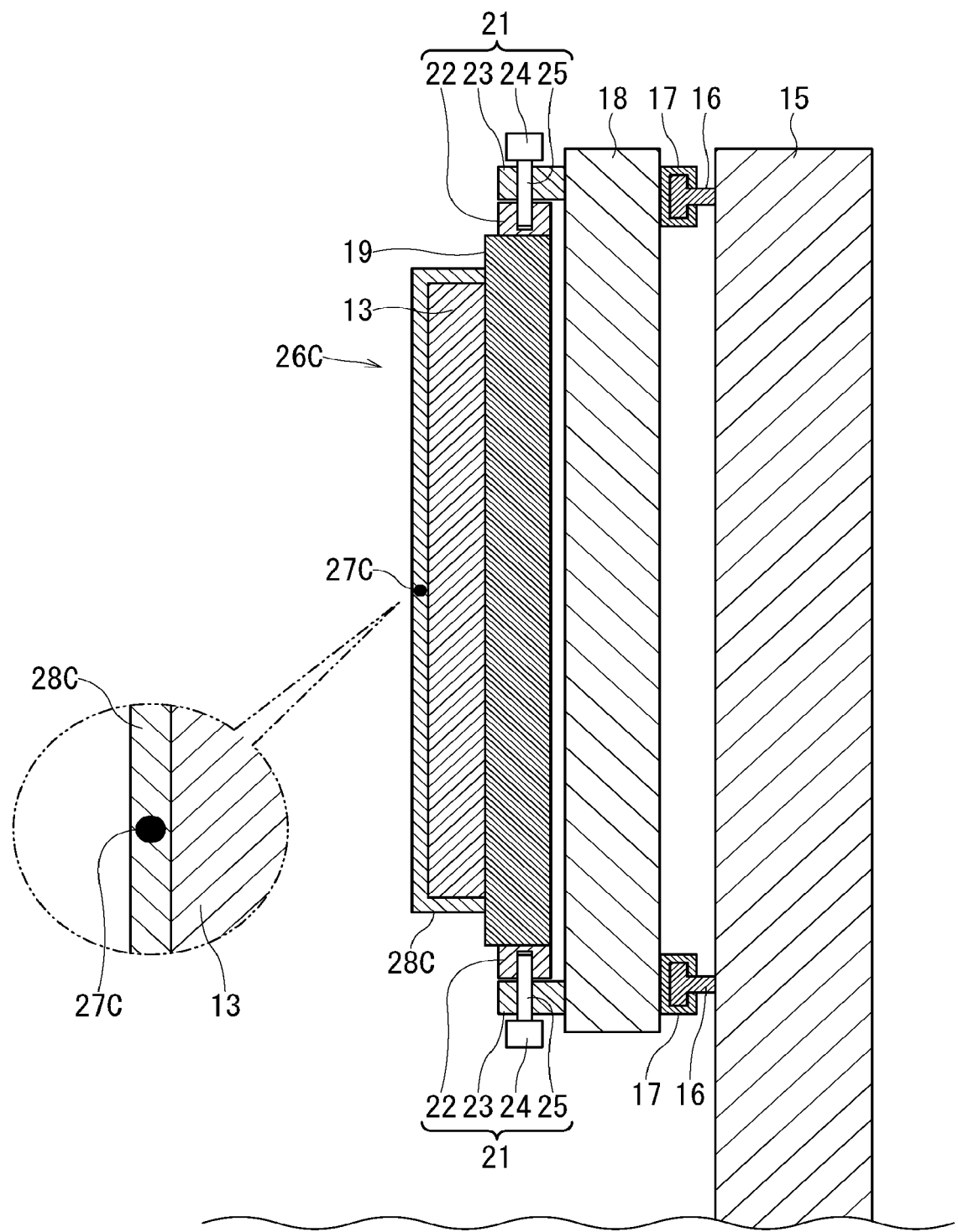
FIG. 11 is a side cross-sectional view illustrating the position adjustment device according to the fourth embodiment.
Figure 12:
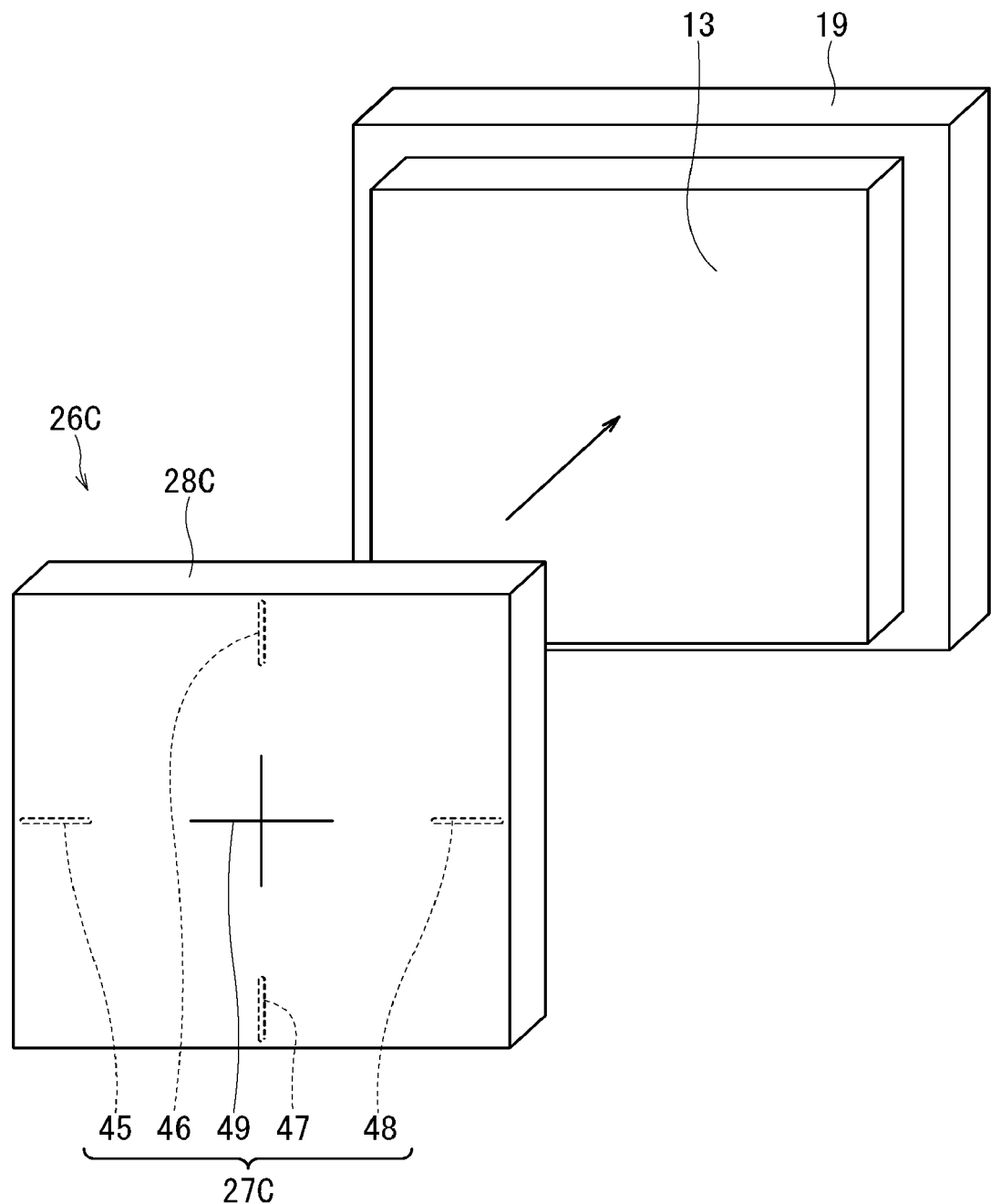
FIG. 12 is a perspective view illustrating the position adjustment device according to the fourth embodiment.

As shown in FIG. 11 and FIG. 12, the position adjustment device 26C according to the fourth embodiment has a substantially C-shape in a side cross-sectional view and is a box-shaped member opened on the back side. The position adjustment device 26C is configured to interdigitate with (i.e., fit into) the flat panel detector 13. The position adjustment device 26C includes a guide 27C provided on the front side and a fixing member 28C having a box shape to be fitted into the flat panel detector 13. The position adjustment device 26C is detachably attached to the flat panel detector 13.

The fixing member 28C is made of synthetic resin that is not depicted in an X-ray image. The four sides of the fixing member 28C are fixed to the flat panel detector 13 or the moving portion 19. Here, the fixing member 28C may be screwed or may be fixed by using a predetermined clamp. A latching piece to be latched by the flat panel detector 13 or the moving portion 19 may be provided on each of the four sides of the fixing member 28B.

The guide 27C according to the fourth embodiment is composed of the first markers 45, 46, 47, and 48 depicted in the X-ray image and the second marker 49 that can be measured by the optical device 7. As shown in the partially enlarged view of FIG. 11, the first markers 45, 46, 47, and 48 are composed of wires embedded in the front side of the fixing member 28C. As shown in FIG. 12, the four first markers 45, 46, 47, and 48 are embedded in the front side of the fixing member 28C.

Each of the first markers 45, 46, 47, and 48 is formed in such a linear shape that the two axes of the two-dimensional coordinates corresponding to the surface of the flat panel detector 13 can be specified by an X-ray image. The intersection angle between virtual lines obtained by extending the respective wires is 90 degrees. The intersection point of the virtual lines is provided so as to correspond to the substantially central position of the flat panel detector 13.

The second marker 49 is a portion printed on the front side of the fixing member 28C with a paint that does not appear in an X-ray image. The second marker 49 is composed of two lines, one of the two lines extends so as to correspond to the transverse direction (i.e., X-axis) of the flat panel detector 13, and the other of the two lines extends so as to correspond to the longitudinal direction (i.e., Y-axis) of the flat panel detector 13. The two lines are arranged in a cross shape.

In addition, the intersection angle between the two lines arranged in a cross shape is 90 degrees. Further, these two lines are provided such that the intersection point of these two lines corresponds to the substantially central position of the flat panel detector 13. Each of these lines is formed in such a straight line that the two axes of the two-dimensional coordinates corresponding to the surface of the flat panel detector 13 can be measured by the optical device 7.

In the fourth embodiment, the intersection point of the virtual lines obtained by extending the respective first markers 45, 46, 47, and 48 matches the intersection point of the lines of the second marker 49. Since the first markers 45, 46, 47, and 48 are embedded in the fixing member 28C and the second marker 49 is printed on the fixing member 28C, the respective positions of the first markers 45, 46, 47, and 48 and the second marker 49 are fixed to each other.

When the X-rays are radiated under the state where the position adjustment device 26C is attached to the flat panel detector 13, the images of the first markers 45, 46, 47, and 48 of the guide 27C appear in the X-ray image. In other words, the position P2 (FIG. 8) of the intersection point of the first markers 45, 46, 47, and 48 of the guide 27C can be specified by the X-ray image. Further, the position P2 of the intersection point of the lines of the second marker 49 of the guide 27C can be measured by the optical device 7.

The other positions including the first position P1, the third position P3, the first difference D1, the second difference D2, and the third difference D3 are the same as those of the above-described second embodiment (FIG. 8). By specifying the third difference D3, the positional deviation amount between the first position P1 corresponding to the isocenter C and the third position P3 that is the image center of the flat panel detector 13 is grasped. Accordingly, an operator measures the guide 27C by using the optical device 7, and operates the operation units 24 of the respective position adjusters 21 as the position adjustment unit so as to move the flat panel detector 13 while checking the second position P2.

In the fourth embodiment, the plural wires embedded in the fixing member 28C are the plural first markers 45, 46, 47, and 48 to be depicted in the X-ray image. When the position adjustment device 26C is attached to the flat panel detector 13, the first markers 45, 46, 47, and 48 are provided on the peripheral portion of the flat panel detector 13.

In this manner, since the plural markers 45, 46, 47, and 48 to be depicted in the X-ray image are not positioned at the image center of the flat panel detector 13, the markers 45, 46, 47, and 48 do not become an obstacle to imaging when the patient K as an object is imaged for generating the X-ray image. In other words, in the fourth embodiment, after the position adjustment of the flat panel detector 13 with the use of the position adjusters 21, it is not required to detach the position adjustment device 26C from the flat panel detector 13.

In the fourth embodiment, each of the first markers 45, 46, 47, and 48 depicted in the X-ray image and the second marker 49 measurable by the optical device 7 can be provided at appropriate positions. For instance, the first markers 45, 46, 47, and 48 can be provided at positions that are not obstructive at the time of X-ray imaging of the object and the second marker 49 can be provided at a position that can be easily measured by using the optical device 7.

Fifth Embodiment

Next, the position adjustment device 26D for the flat panel detector according to the fifth embodiment will be described by referring to FIG. 13 and FIG. 14. Note that the same reference signs are assigned to the same components as the above-described embodiment in each figure, and duplicate description is omitted. In the following description, it is assumed that the left side of the sheet of FIG. 13 is the front side (i.e., anterior side) of the flat panel detector 13 and the position adjustment device 26D.

Figure 13:
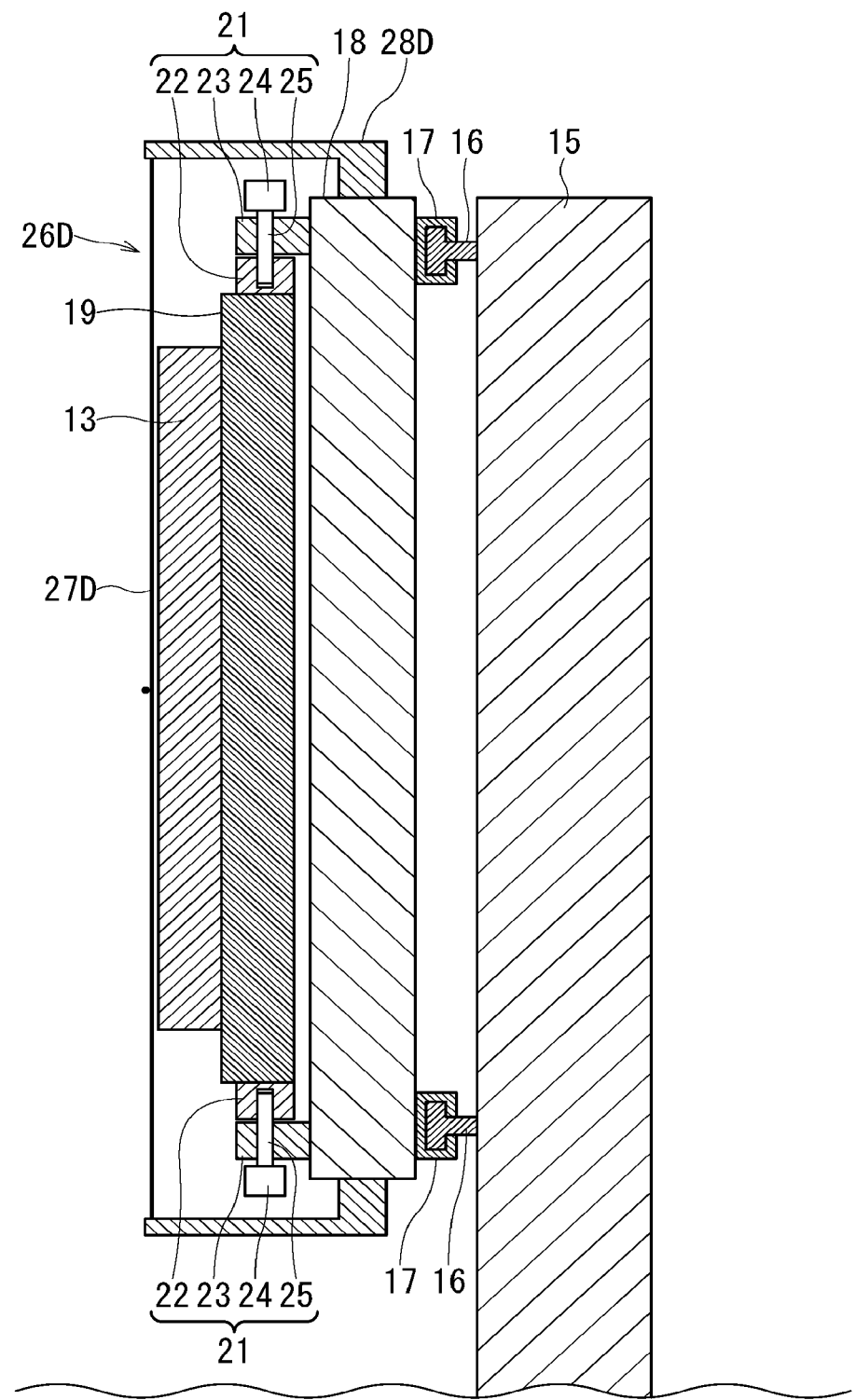
FIG. 13 is a side cross-sectional view illustrating the position adjustment device according to the fifth embodiment.
Figure 14:
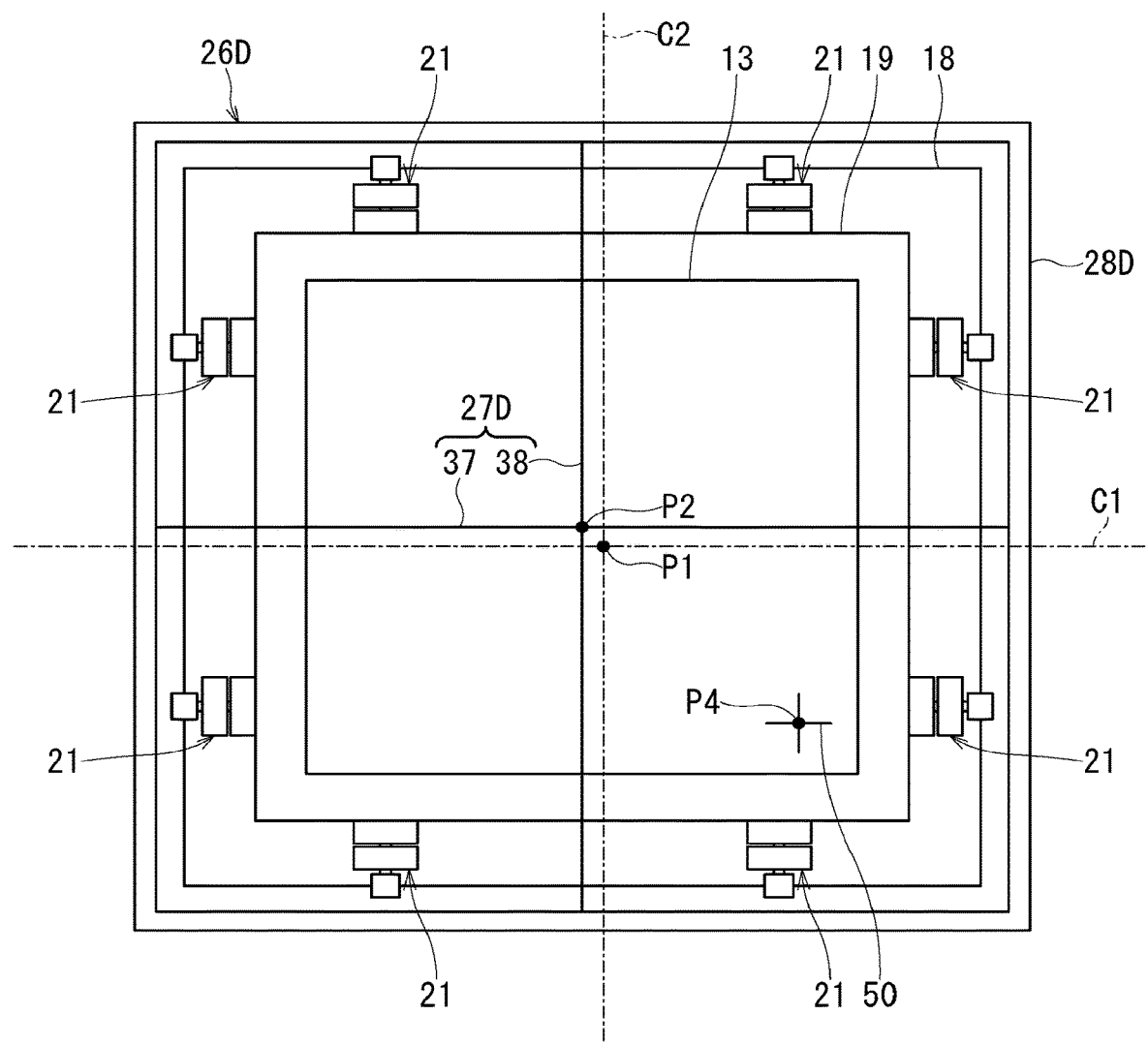
FIG. 14 is a front view illustrating the position adjustment device according to the fifth embodiment.

As shown in FIG. 13 and FIG. 14, the position adjustment device 26D according to the fifth embodiment includes a guide 27D to be in contact with the surface of the flat panel detector 13 and a fixing member 28D fixed to the periphery of the support portion 18.

The guide 27D is composed of wires 37 and 38. The wire 37 extends so as to correspond to the transverse direction (i.e., X-axis) of the flat panel detector 13, and the wire 38 extend so as to correspond to the longitudinal direction (i.e., Y-axis) of the flat panel detector 13. These wires 37, 38 are made of metal to be depicted in an X-ray image, and can be measured by the optical device 7.

The fixing member 28D of the fifth embodiment is fixed to the support portion 18. In other words, the fixing member 28D is fixed to the second member 23 on the support portion side of each position adjuster 21. Here, the fixing member 28D may be screwed to the support portion 18 or may be fixed by using a predetermined clamp.

When X-rays are radiated under the state where the position adjustment device 26D is attached to the flat panel detector 13, the image of the guide 27D appears in the X-ray image. In other words, the position P2 (FIG. 5) of the intersection point of the wires 37 and 38 of the guide 27D can be specified by the X-ray image.

The other positions including the first position P1, the third position P3, the first difference D1, the second difference D2, and the third difference D3 are the same as those of the above-described first embodiment (FIG. 5). By specifying the third difference D3, the positional deviation amount between the first position P1 corresponding to the isocenter C and the third position P3 that is the image center of the flat panel detector 13 is grasped. Accordingly, an operator measures the guide 27D by using the optical device 7, and operates the operation units 24 of the respective position adjusters 21 as the position adjustment unit so as to move the flat panel detector 13 while checking the second position P2.

At a predetermined position on the surface of the flat panel detector 13 according to the fifth embodiment, there is provided a panel marker 50 printed with a paint that does not appear in an X-ray image. The panel marker 50 is composed of two lines, one of the two lines extends so as to correspond to the transverse direction (i.e., X-axis) of the flat panel detector 13, and the other of the two lines extends so as to correspond to the longitudinal direction (i.e., Y-axis) of the flat panel detector 13. The two lines are arranged in a cross shape. The intersection point of the two lines is defined as the fourth position P4.

The fourth position P4 is a position that can be measured by the optical device 7. The fourth position P4 is used to specify the movement amount of the flat panel detector 13 when the operator operates the operation units 24 of the position adjusters 21 to move the flat panel detector 13.

When performing adjustment by using the optical device 7, the operator can move the flat panel detector 13 with reference to the second position P2 based on the guide 27D. For instance, the flat panel detector 13 is moved such that the moving direction and the moving distance of the fourth position P4 match the direction and the distance corresponding to the third difference D3 with reference to the second position P2.

In addition, the operator can move the flat panel detector 13 with reference to the first position P1 based on the isocenter C. For instance, the flat panel detector 13 is moved such that the moving direction and the moving distance of the fourth position P4 match the direction and the distance corresponding to the third difference D3 with reference to the first position P1.

In the fifth embodiment, the flat panel detector 13 is attached before the position adjustment of the flat panel detector 13 with the use of the position adjusters 21. After adjusting the position of the flat panel detector 13 by using the position adjusters 21, the position adjustment device 26D is detached from the flat panel detector 13.

Although the position adjustment devices for the flat panel detector according to the possible embodiments has been described on the basis of the first to fifth embodiments, the configuration applied in any one of the embodiments may be applied to other embodiments and the configurations applied in each embodiment may be used in combination. For instance, the configuration in which the guide of the fifth embodiment is fixed to the support portion may be applied to the guide of each of the second to fourth embodiments.

In the above-described embodiments, the two axes (X-axis and Y-axis) of the two-dimensional coordinates corresponding to the surface of the flat panel detector 13 are included in a vertical plane that is perpendicular to the horizontal plane (i.e., floor surface). Thus, the transverse axis C1 of the isocenter C forms the horizontal axis, and the longitudinal axis C1 of the isocenter C forms the vertical axis. In other words, the transverse axis C1 and the longitudinal axis C1 of the isocenter C respectively coincide with the horizontal axis and the vertical axis. When the flat panel detector 13 is installed so as to be inclined with respect to the vertical plane, it is not required that the transverse axis C1 and the longitudinal axis C1 of the isocenter C respectively match the horizontal axis and the vertical axis.

Although the flat panel detector 13 is used as a medical-related device in the above-described embodiments, the position adjustment device 26 may be used for position adjustment of the flat panel detector 13 other than the medical-related device. For instance, the flat panel detector 13 may be used for radiation penetration inspection performed as a part of non-destructive inspection, geological survey for investigating fossils, counseling investigation of art works, scientific investigation, or investigation of archeological artifacts. Further, the position adjustment device may be used for positioning for a radiation detector or particle beam detector, e.g., may be used for accurately setting scintillation or foam box with respect to a certain reference. In other words, the imaging target may be a person or a non-living object.

When calibration of various devices is performed by using the X-ray image or the optical device 7, a calibration phantom may be installed at the isocenter C.

Although the guide 27 is in contact with the surface of the flat panel detector 13 in the above-described embodiments, there may be a gap between the guide 27 and the surface of the flat panel detector 13. In other words, it is sufficient that the guide 27 is close to the surface of the flat panel detector 13. Further, the guide 27 may be attached to the surface of the flat panel detector 13 in a non-detachable manner.

In the position adjustment work with the use of the position adjustment device 26, X-ray imaging and movement of the flat panel detector 13 are not alternately repeated. In other words, although the position adjustment of the flat panel detector 13 has been completed by X-ray imaging for generating one image, X-ray imaging for generating one image and movement of the flat panel detector 13 may be alternately repeated. Even in such a case, the number of X-ray imaging is greatly reduced as compared with the conventional technology.

Although the image center of the flat panel detector 13 is set as the third position P3 and this third position P3 is made to coincide with the first position P1 corresponding to the isocenter C in the above-described embodiments, this is only one aspect and embodiments of the present invention is not limited to such an aspect. For instance, the third position P3 does not need to be the image center of the flat panel detector 13, and it is sufficient that the third position P3 is a portion where the lesion area of the patient K is depicted in the image.

Although the third position P3 as the image center of the flat panel detector 13 is the intersection point of the central horizontal axis 41 and the central longitudinal axis 42 of the flat panel detector 13 in the above-described embodiments, it is not necessarily required that the third position P3 is the intersection between the central horizontal axis 41 and the central longitudinal axis 42 of the flat panel detector 13. It is sufficient that the third position P3 is a portion where a target to be imaged under X-ray imaging is positioned.

Although a wire is used as a guide in the above-described present embodiments, a configuration other than a wire may be used. For instance, the guide may be formed by using plural metal spheres to be depicted in an X-ray image.

According to one of the embodiments described above, by providing the fixing portion for fixing the guide to either the flat panel detector side or the support portion side of the position adjustment unit, the work efficiency of the position adjustment of the flat panel detector can be improved.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A position adjustment device for a flat panel detector comprising:
    a guide that is provided on a surface side of the flat panel detector and can be measured by an optical device; and
    a fixing member configured to fix the guide to one of a side of the flat panel detector of a position adjustment unit and a side of a support portion for supporting the flat panel detector, the position adjustment unit being provided between the flat panel detector and the support portion,
    wherein the position adjustment unit is configured to include a first member fixed to the flat panel detector, a second member fixed to the support portion, and an operation unit for adjusting a distance between the first member and the second member,
    the fixing member is configured to fix the guide to one of the first member and the second member, and
    the operation unit is configured to match a position corresponding to the isocenter with a position that is an image center of the flat panel detector, by adjusting the distance between the first member and the second member.

2. The position adjustment device for a flat panel detector according to claim 1,
    wherein the guide is close to a surface of the flat panel detector.

3. The position adjustment device for a flat panel detector according to claim 1,
    wherein the guide is formed in such a straight line that two axes of two-dimensional coordinates corresponding to a surface of the flat panel detector can be measured by the optical device.

4. The position adjustment device for a flat panel detector according to claim 1,
    wherein the guide includes plural markers that can measure two axes of two-dimensional coordinates corresponding to a surface of the flat panel detector by using the optical device.

5. The position adjustment device for a flat panel detector according to claim 1,
    wherein the guide includes plural markers that are provided at a periphery of the flat panel detector and are depicted in an X-ray image.

6. The position adjustment device for a flat panel detector according to claim 1,
    wherein the guide includes a first marker depicted in an X-ray image and a second marker, position of which can be measured by the optical device.

7. The position adjustment device for a flat panel detector according to claim 1, wherein the guide includes a wire.

8. The position adjustment device for a flat panel detector according to claim 1,
wherein the guide is fixed to the flat panel detector.

9. The position adjustment device for a flat panel detector according to claim 1,
wherein the guide is fixed to the support portion.

10. A position adjustment method for a flat panel detector comprising:
providing a guide on a surface side of the flat panel detector, the guide being depicted in an X-ray image and being positionally measurable by an optical device;
fixing the guide to one of a side of the flat panel detector of a position adjustment unit and a side of a support portion for supporting the flat panel detector, the position adjustment unit being provided between the flat panel detector and the support portion,
specifying a first difference between a first position corresponding to an isocenter and a second position indicated by the guide by using the optical device;
specifying a second difference between the second position and the third position, which is an image center of the flat panel detector, by using the X-ray image;
specifying a third difference between the first position and the third position, depending on the first difference and the second difference; and
operating the position adjustment unit according to the third difference in such a manner that the third position matches the first position.

11. A radiotherapy apparatus comprising:
the position adjustment device for a flat panel detector according to claim 1;
an X-ray imaging apparatus configured to generate an X-ray image of an object by irradiating the flat panel detector with X-rays; and
a radiation irradiation apparatus configured to irradiate the object with therapeutic radioactive rays.

* * * * *